United States Patent [19]

Schechter et al.

[11] Patent Number: 5,281,519
[45] Date of Patent: Jan. 25, 1994

[54] SIMPLE, RAPID AND RELIABLE METHOD FOR DETECTING THALASSEMIA

[75] Inventors: Alan N. Schechter, Bethesda, Md.; Shu-Zhen Huang, Shanghai, China; Griffin P. Rodgers, Silver Spring, Md.

[73] Assignee: The United States of America as represented by the Department of Health and Human Services, Washington, D.C.

[21] Appl. No.: 965,513

[22] Filed: Oct. 23, 1992

Related U.S. Application Data

[63] Continuation of Ser. No. 507,645, Apr. 11, 1990.

[51] Int. Cl.⁵ .................... C12Q 1/68; C12P 19/34
[52] U.S. Cl. .......................... 435/6; 935/77; 935/78
[58] Field of Search ............. 435/6, 91; 935/77, 78

[56] References Cited

U.S. PATENT DOCUMENTS 4,683,195 7/1987 Mullis et al. .................. 435/6

OTHER PUBLICATIONS

Kazazian, Jr. et al., PNAS (USA) 72(2):567-571 (Feb. 1975).
Maniatis et al. Molecular Cloning & Laboratory Manual, Cold Spring Harbor Lab., NY, 1982, pp. 188-189.
Bethesda Research Labs Catalog & Reference Guide, 1988, p. 139.
Saiki et al., The New Engl. J. Med. 319(9):537-541 (Sep. 1, 1988).

Primary Examiner—Stephanie W. Zitomer
Attorney, Agent, or Firm—Morgan & Finnegan

[57] ABSTRACT

A simple, rapid and reliable method for diagnosis of thalassemia is described. The method comprises amplification of the cDNA by polymerase chain reaction and determining the ratio between $\alpha$ and $\beta$ hemoglobin chain mRNAs.

7 Claims, 11 Drawing Sheets

NORMAL      $\beta^0$-THALASSEMIA      $\beta^+$-THALASSEMIA

Figure 6b

NORMAL      $\beta^0$-THALASSEMIA      $\beta^+$-THALASSEMIA

SIMPLE, RAPID AND RELIABLE METHOD FOR DETECTING THALASSEMIA

This is a continuation of co-pending application Ser. No. 07/507,645, filed on Apr. 11, 1990.

The present invention is related generally to diagnostic methodologies. More particularly, the present invention is related to a simple, inexpensive and rapid method for detecting thalassemias and monitoring therapeutic effects on the disease.

BACKGROUND OF THE INVENTION

The thalassemias represent a heterogeneous group of diseases, characterized by the absence or diminished synthesis of one or the other of the globin chains of hemoglobin A. In $\alpha$-thalassemia, $\alpha$-chain synthesis is decreased or absent; whereas in $\beta$-thalassemia, $\beta$-chain synthesis is diminished or absent. Numerous molecular defects account for the various thalassemias. The degree of clinical expression is generally dictated by the nature and severity of the underlying globin gene (DNA) defect. Thalassemia major (homozygous $\beta$-thalassemia) defines the most severe variety of the disease. Thalassemia intermedia and thalassemia minor refer to the heterozygous state, generally associated with milder clinical manifestations.

Beta-thalassemia is an autosomal recessive disorder characterized by absent ($\beta^o$) or decreased ($\beta^+$) synthesis of the $\beta$-globin chain. Thalassemia is found in almost all population and ethnic groups around the world. It has been estimated that 3% of the world's population or 150 million people carry $\beta$-thalassemia genes. Indeed, it is among the most common genetic diseases in the world. Alpha thalassemia, the corresponding disorder of $\alpha$ hemoglobin chain is also of great prevalence, especially in the Orient.

By the next century, probably over 50% of the world population in certain groups will be at risk for the thalassemias. Thus, in world terms, the problem would be anticipated to increase with time. Because these predictions have tremendous medical, social and economic implications, particularly in developing nations, a major challenge to health professionals is the development of methodologies for molecular diagnosis of the thalassemia syndromes that are simple and reliable, especially those that do not depend on radioactivity. Such a strategy would allow for detection, as well as facilitate genetic counseling of carriers.

Traditional detection of $\beta$-thalassemia has relied heavily on the hematological tests. With the more generalized use of electronic cell counters, the diagnosis is first suspected by the discovery of a low MCV and MCH on routine "complete" blood counts. Increased levels of HbA$_2$ (to 4–6 percent) and/or increased HbF (up to 5-20 percent) demonstrated by quantitative hemoglobin electrophoresis supports the diagnosis. Unfortunately, the differential diagnosis between iron deficiency anemia and $\beta$-thalassemia trait can be difficult in practice, if there are not reciprocal increases in HbA$_2$ and/or HbF. Moreover, in the presence of concomitant iron-deficiency, HbA$_2$ levels in $\beta$-thalassemic individuals may fall into the normal range. Occasionally, the diagnosis of iron deficiency cannot be made on the basis of measurements of serum iron, iron binding capacity and/or the absence of stainable iron in the bone marrow. In these instances, the demonstration of a reduced $\beta$-globin synthetic rate (compared to $\alpha$-globin), generally employing $^3$H-leucine to analyze globin chain production in reticulocytes is required for a conclusive diagnosis. This procedure is cumbersome and not well-suited for large scale investigations.

Recently, with improvements in techniques in molecular biology and with the cloning of the human globin genes, cloning and sequencing the $\beta$ globin genes from a patient with suspect $\beta$ thalassemia (or the $\alpha$ globin gene from patients suspected to have alpha thalassemia) have become possible. More recently, it has been found that a number of point mutations that result in the thalassemic phenotype are genetically linked to specific restriction fragment length polymorphisms or haplotypes. Thus, by isolating DNA from peripheral tissues (usually leukocytes), one can perform restriction enzyme digestion of genomic DNA and Southern blotting to examine for the presence of specific haplotypes from which one can infer the particular thalassemic mutation. However, the linkage of different $\beta$-globin gene cluster haplotypes with specific mutations giving rise to the $\beta$-thalassemia is not definitive. Moreover, the isolation, cloning and sequencing of the defective $\beta$-globin gene(s) in suspected carriers is time-consuming and not well suited for large population studies.

SUMMARY OF THE INVENTION

It is, therefore, an object of the present invention to provide a simple, rapid and reliable method, without in vivo use of radioactive material, for the diagnosis of thalassemias.

It is a further object of the present invention to provide a method useful for planning treatment and prevention, genetic counselling as well as the study of gene regulation and expression, and the observation of therapeutic effects in thalassemias.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1—Analysis of purity of RNA isolated from whole blood mononuclear cells using the VRC method. RNA was electrophoresed in 1% Seakem agarose gels.
Lane 1-4: Normal subjects
Lane 5: Patient with $\beta$-thalassemia major
M.W. 123 bp ladder DNA marker FIG. 2—A map of the positions and orientations of the oligonucleotide primers used in the reverse transcription and co-amplification of the alpha/beta 4 and beta 1/gamma mRNAs. The size of the PCR products are 372/490 bp and 422/489 bp, respectively.

A map of the alpha (FIG. 2a) and beta (FIG. 2b) globin cluster are shown in the first line. A schematic of the alpha, beta, and gamma mRNAs is shown in the second line.

Amplification products were electrophoresed on 3% NuSieve agarose gel in TBE buffer, stained by ethidium bromide. The picture was taken on U. V lamp using Polaroid #55 film. The positive and negative pictures were obtained simultaneously.

A photograph of the co-amplification products run on a 3% NuSieve agarose gel and stained with ethidium bromide; the negative of the photograph was scanned on a laser densitometer. The heights of the peaks represent the relative intensities of specific co-amplification products.

FIG. 6—A comparison of the patterns of PCR products from adults, $\beta^o$ thalassemia major and $\beta^+$ thalassemia major patients with specific Group I and Group II primers.

In normal adults there are $\alpha$ and $\beta$ peaks and no or a small $\tau$ peak. In $\beta^o$ thalassemia major, there are $\alpha$ and $\tau$ peaks, but no $\beta$ peak. In $\beta^+$ thalassemia, there are $\alpha$ and $\tau$ peaks, and also a small $\beta$ peak.

According to the lengths of the PCR products with alpha (371 bp) and gamma (489 bp) specific primers, the $\beta$ primer was chosen. Group I ($\alpha+\beta 4$, 372 bp+490 bp) and Group II ($\beta 1+\gamma$, 422 bp+489 bp) were optimal.

M.W.: 1 kb ladder DNA marker.

DETAILED DESCRIPTION OF THE INVENTION

The above and various other objects and advantages of the present invention are achieved by a new method for diagnosing thalassemia, comprising the steps of (a) preparing RNA from reticulocytes of the peripheral blood of an individual suspected of thalassemia; (b) preparing cDNA from the RNA obtained from step (a); and then (c) quantitating the cDNA prepared in step (b) with polymerase chain reaction (PCR) using suitable primers and determining the ratio of $\alpha$ and $\beta$ mRNA by comparing the densitometric or radiometric ratio between the corresponding cDNAs.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed or contemplated herein are standard methodologies well known to one of ordinary skill in the art. The methods, materials, and examples are illustrative and not limiting.

MATERIALS AND METHODS

Preparation of Cells from human whole blood

Reticulocyte RNA was isolated from peripheral blood of ten normal individuals and seven patients with $\beta$ thalassemia major (five with $\beta^o$ thalassemia and two with $\beta^+$ thalassemia) and two patients with -thalassemia (one with -thalassemia-1 and another with Barit's Hydrops), and one patient with sickle cell anemia treated with hydroxyurea at 0, 57 and 88 days. RNA was isolated after separating the mononuclear cells from erythrocytes. Mononuclear cells from 7 ml of the anticoagulation diluted blood (1 ml blood was diluted with 1 ml cold phosphate-buffered saline PBS) were isolated over 7 ml of LSM (Lymphocyte Separation Medium, Organon Teknika Corporation #36427), by centrifugation for 30 minutes at room temperature (about 22°-24° C.). The mononuclear cells at the interface were collected and washed twice in cold PBS buffer before RNA extraction.

Preparation of RNA and DNA

RNA and DNA were isolated simultaneously from the cells by the VRC method (Vanadyl Ribonucleoside Complex, BRL #5522SA). 1×10⁷ blood cells in an Eppendorf tube were centrifuged briefly and to each cell pellet was added 200 µl of RSB/VRC solution (RSB:VRC:DEPC.H₂O=2:1:17, 10×RSB:100 mM Tris·HCl, pH 7.5/100 mM NaCl/30 mM MgCl₂) and then 20 µl of 10% Np40 (Nonionic detergent, Sigma #N3516). After mixing vigorously, samples were kept on ice, then spun for 15 seconds in an Eppendorf centrifuge (Model 541SC). RNA was then isolated from the supernatants and DNA was isolated from the pellets.

Isolation of RNA

Figure 3:
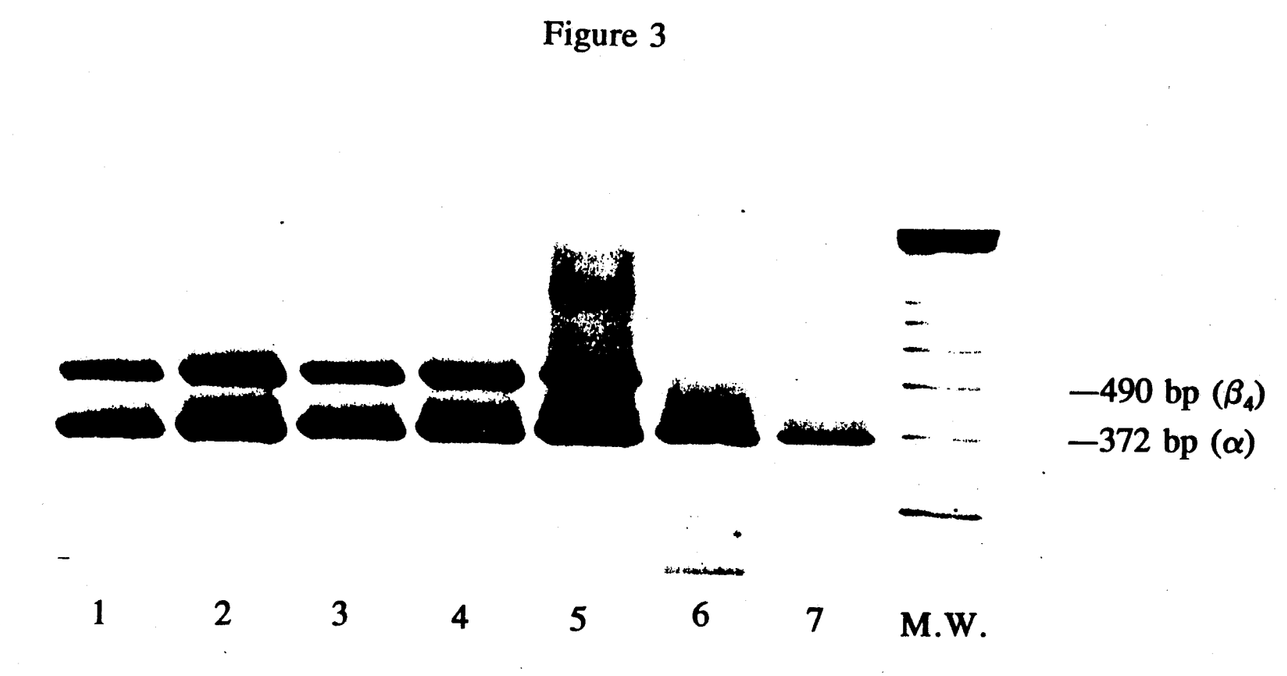
FIG. 3—Analysis of co-amplification products of alpha and beta globin mRNAs with alpha/beta 4-specific primers.
Lane 1-5: Normal adults
Lane 6-7: Patients with $\beta^o$ thalassemia (major)
M.W. 123 bp ladder DNA marker The alpha mRNAs are present in all normal adults and patients with B thalassemia major. Beta mRNA is only present in normal adults but not in the cells of $\beta^o$ thalassemia major patients.

The supernatant was spun again for 5 minutes and transferred to a new Eppendorf tube. Two hundred microliter of 2×Lysate buffer (1% SDS/0.6M NaCl/10 mM EDTA/20 mM Tris·HCl, pH 7.5) was added to this new tube for RNA isolation. The RNA was extracted twice in 1 volume of supersaturated phenol, then chloroform/isoamyl alcohol 24:1). Aqueous phase was precipitated in 2.5 volume of cold absolute ethanol and frozen on dry ice for 20 minutes. The RNA pellet was washed twice with 80% ethanol and dried in a vacuum centrifuge for 5 minutes, and dissolved in DEPC.H₂O (diethylpyrocarbonate treated water). 1 µg of RNA was subjected to gel electrophoresis at 100 V for 1 hr in 1% Seakem ME agarose gel (FMC #50013) (FIG. 3).

Isolation of DNA

The cell pellet was resuspended in 200 µl of TE(pH 7.5), 200 µl of 2×Lysate buffer and 10 µl of proteinase K (10 mg/ml, BRL #5530UA) and the digestion was done for 3 hours or overnight at 37° C. The following steps were the same as that for RNA extraction, except DNA pellet was dissolved in TE (pH 7.5).

Oligonucleotides design and synthesis

The sequence of each of the oligonucleotide primers used in this study are shown in Table 1.

Four sets of primers were designed: $\alpha$, $\beta1$, $\beta4$ and $\gamma$. All of them were chosen from sequences within the globin gene exon for cDNA amplification. These four sets of primers were divided into two groups. Group I consisted of $\alpha$ and $\beta4$ primers, and the length of PCR products should be 372 bp ($\alpha$) and 490 bp ($\beta4$). Group II consisted of $\beta1$ and $\gamma$ primers, it was 422 bp ($\beta1$) and 489 bp ($\gamma$).

The oligonucleotide primers were synthesized in an Applied Biosystems 380 B DNA Synthesizer and gel-purified.

cDNA synthesis

RNA was isolated from whole blood of the ten normal adults and six patients of $\beta$ thalassemia major as described above. 2 µg RNA was transferred to each 1.5 ml Eppendorf tube and 3 µl of 5× buffer (250 mM Tris·HCl, pH 8.3, 375 mM KCl, 15 mM MgCl₂ and 50 mM dithiothreitol), 1 µl of 10 mM dNTP mix (10 mM dATP, dCTP, dGTP and TTP), 0.5 µl of OligodT₁₂₋₁₈ (0.5 mg/ml, BRL) or hexanucleotide primer (n=6, New England Biolabs) and 0.5 µl of m-MLV reverse transcriptase (200 U/µl, BRL) were added. DEPC.H₂O was used to make a total volume of 15 µl which was incubated at 37° C. for 30 minutes, followed by heating at 95° C. for 5 minutes, then put on ice immediately and cooled to 4° C.

PCR co-amplification of cDNA

The above cDNA samples (15 µl) were centrifuged for 30 seconds. Each 7 µl of cDNA were transferred into two new Eppendorf tubes, marked I and II. Group I ($\alpha+\beta4$) and Group II ($\beta1+\gamma$), or group III ($\alpha+\beta1+\gamma$) if necessary, of primers were added to tubes I, II and III, respectively. Then 2.5 µl of 10×buffer (vide infra), 2 µl of 10 mM dNTP, 0.5 µof Taq. polymerase (5 U/µl, Perkin Elmer Cetus) or 1 µl of *Thermus aquaticus* DNA polymerase (2.5 U/µl, New England Biolabs #252) were added to each tube. H₂O was added to bring to a final volume of 25 µl. For comparison, 0.5 µl of ³²p-dCTP (vide infra) was added to each above tube to test the counts from gel. The cDNA mixture was covered with 15 µl of mineral oil. PCR amplification of cDNA samples was done on a Perkin-Elmer-Cetus DNA thermal cycler machine for 40 cycles: melting at 94° C. for 1.5 minutes, annealing at 55° C. for 2 minutes and extending at 72° C. for 3 minutes; then kept at 4° C. PCR products were precipitated by ethanol and redissolved in TE(pH 7.5), if the ³²p-dCTP was added.

10×buffer:
1. Perkin Elmer Cetus: 500 mM KCl, 100 mM Tris·HCl, pH 8.3, 15 mM MgCl₂, 0.1% (W/V) gelatin.
2. New England Biolabs: 166 mM (NH₂)SO₄, 670 mM Tris·HCl, pH 8.8 at 25° C., 67 mM MgCl₂, 100 mM α-mercaptoethanol and 1.7 µg/ml BSA.

³²p-dCTP:
Deoxycytidine 5'[α−³²p] triphosphate triethylammonium salt, Amersham, 800 ci/mmol.

Analysis of the PCR Products

Eight microliters of PCR products from each sample were subjected to gel electrophoresis in 3% NuSieve GTG agarose (FMC #50082) in TBE buffer, pH 8.3, 80 V for one hour. After staining with ethidium bromide, both pictures (a positive and a negative) were taken with Polaroid #55 film (NSN #55 positive/negative, 4×5 instant sheet film). The negative film was developed in TBE buffer, then water and dried in air. The negative picture was used to measure the ratio of $\alpha$ and $\beta$ mRNA or $\gamma$mRNA and $\zeta$mRNA. from the densities of $\alpha$ and $\beta$ bands on an LkB 2202 Ultrascan Bromma laser densitometer.

In tests where ³²p-dCTP was used, the radioactivity was measured: the $\alpha$, $\beta$, or $\gamma$ and a blank band of each sample on the NuSieve agarose gel were cut out. Each band was put into a 0.5 ml Eppendorf tube and transferred into a glass bottle. The radioactivity was checked on Liquid scintillation counter (LKB Mallac 1209 Rack Beta, program #4). Relative ratios of $\alpha/\beta_4$ were calculated using the following formula:

$$\alpha/\beta = [(C_\alpha - C_o)/(C_\beta - C_o)] \times F$$

where $C_\alpha$ represents the cpm of $\alpha$ band, $C_\beta$ is the cpm of $\beta$ band, $C_o$ the cpm of the blank and F is the efficiency factor, which is ascertained each time by the $\alpha/\beta$ ratio of the same normal standard sample.

RESULTS

Figure 4:
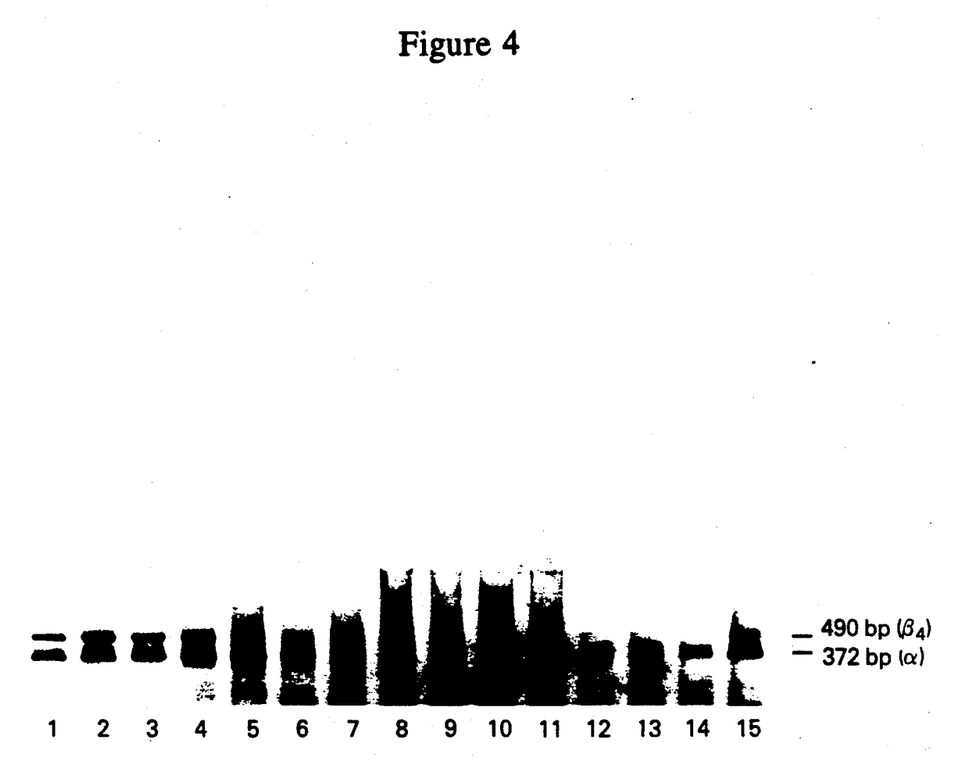
FIG. 4—Analysis of co-amplification products of alpha and beta globin mRNAs with alpha and beta 4 specific primers.
Lane 1-10: Normal adults, $\alpha$ and $\beta$ bands present
Lane 11-14: $\alpha^o$ thalassemia major, $\alpha$ only, no $\beta$ band present
Lane 15: $\beta^+$ thalassemia major, $\alpha$ and a decreased $\beta$ band present FIG. 5—Measurement of co-amplification products of alpha and beta globin mRNAs with alpha and beta 4 specific primers.

FIGS. 3 and 4 show the result of co-amplification of alpha and beta globin mRNA. The amplified fragments show the expected size: $\alpha$ is 372 bp and $\beta4$ if 490 bp. They also show that alpha mRNA is present in normal adult and peripheral blood from the blood of patients and $\beta$ thalassemia major. Alpha globin mRNA is used as a positive internal control for β globin mRNA. Beta globin mRNA is present in normal adult peripheral blood, but not in that of $\beta^o$ thalassemia major patients and is diminished in $\beta^+$ thalassemia. Thus, the diagnosis of β-thalassemia can be confirmed on the mRNA level.

Figure 5:
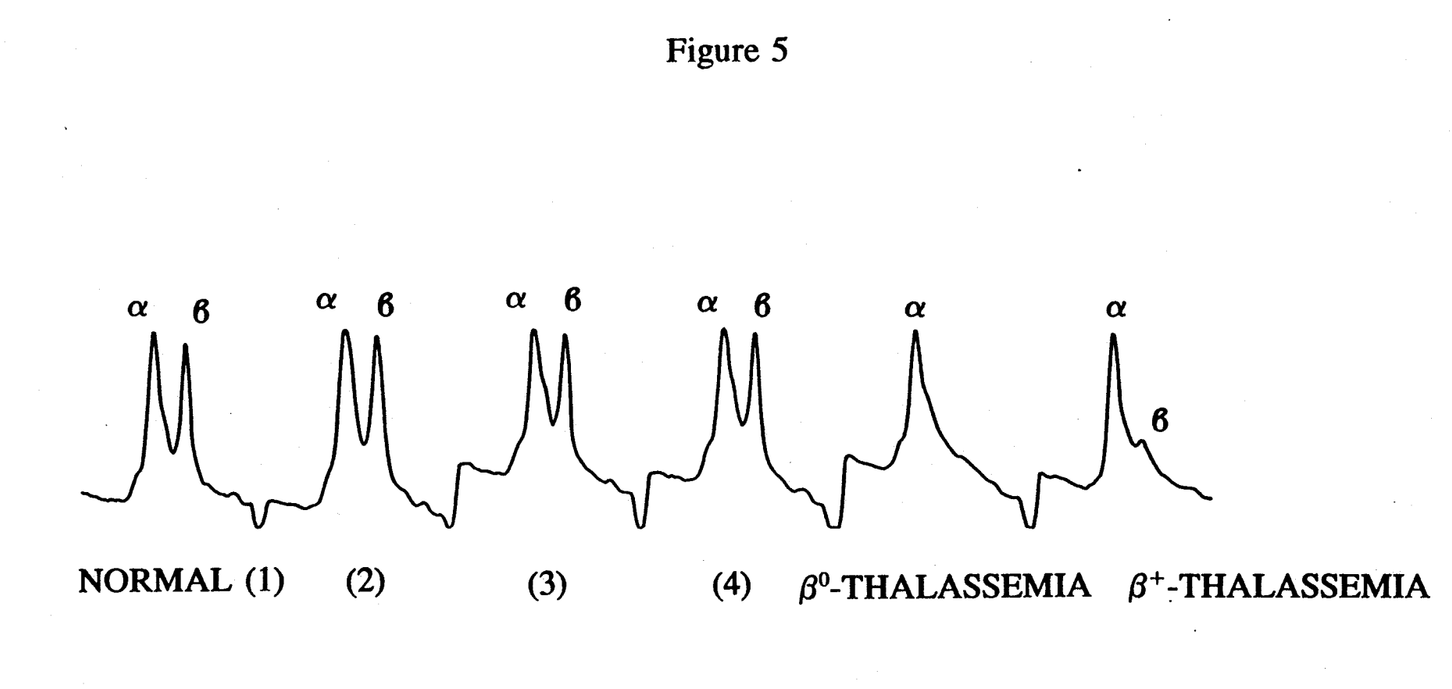
Figure 6A:
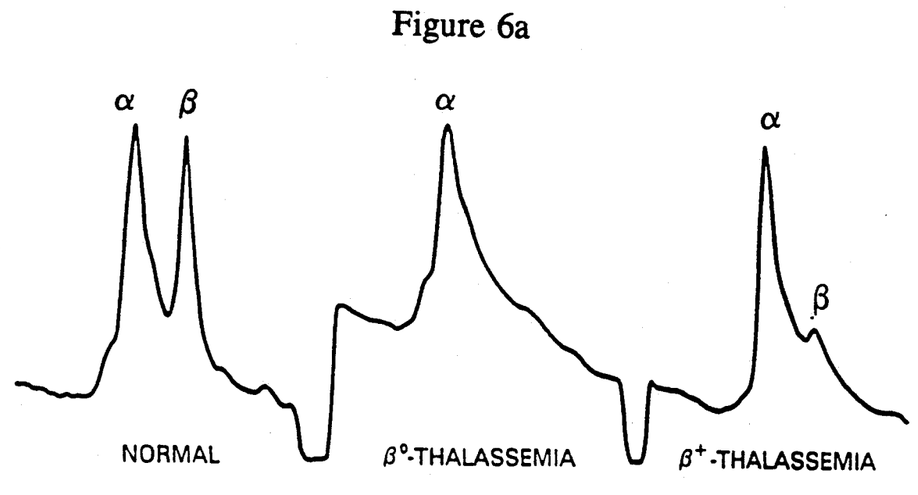
FIG. 6a shows the pattern with Group I primers ($\alpha+\beta 4$)
Figure 6B:
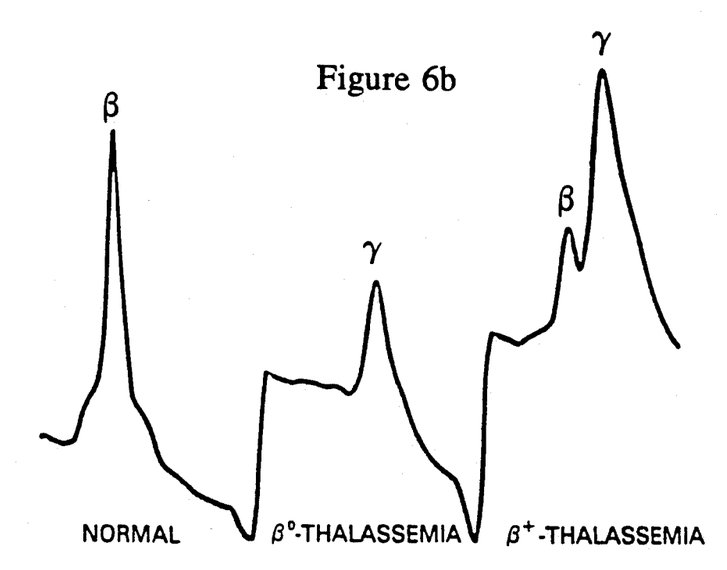
FIG. 6b shows the pattern with Group II primers ($\beta 1+\tau$)

Variations in the relative ratios of alpha to beta in normal subjects and β thalassemia patients were also observed. The ratio of α and β mRNA in normal and β thalassemia subjects are shown in Table 2. The average of α/β from density measurements in normal subjects is about 1.33 (mean ±SE:1.33±0.04) and in $\beta^o$ thalassemia major is >100 (no β band and no β peak) in $\beta^+$ thalassemia major (two cases) is 4.10 (3.6–4.5). The average α/β from radioactivity measurements is about 1.14 (mean ±SE:1.14±0.05) and in $\beta^o$ thalassemia major is about 39.85 (at least 14.4 or greater) in $\beta^+$ thalassemia major (two cases) is 6.10 (5.2–7.2). Thus the differentiation of α/β between normal subjects and β thalassemia major is highly significant. The patterns of α and β mRNA are shown in FIGS. 5 and 6. There are two peaks (α and β) in normal individuals, but only the α peak is seen in the blood of patients with $\beta^o$ thalassemia and a small β peak in $\beta^+$ thalassemia major. FIG. 6 also shows the pattern of β and γ mRNA in normal, $\beta^o$ thalassemia and $\beta^+$ thalassemia subjects. Normally, the γ-mRNA level in adults is approximately 1–2% of total globin mRNA produced. In contrast, γmRNA is compensatorily increased in patients with β-thalassemia as a result of the diminished to absent β-mRNA synthesis. The same results were obtained with the different groups of primers (Group I and Group II). These results are based on the density of α and γ bands (or β/γ bands) as determined in LKB Ultroscan laser densitometer using negative film.

Figure 7:
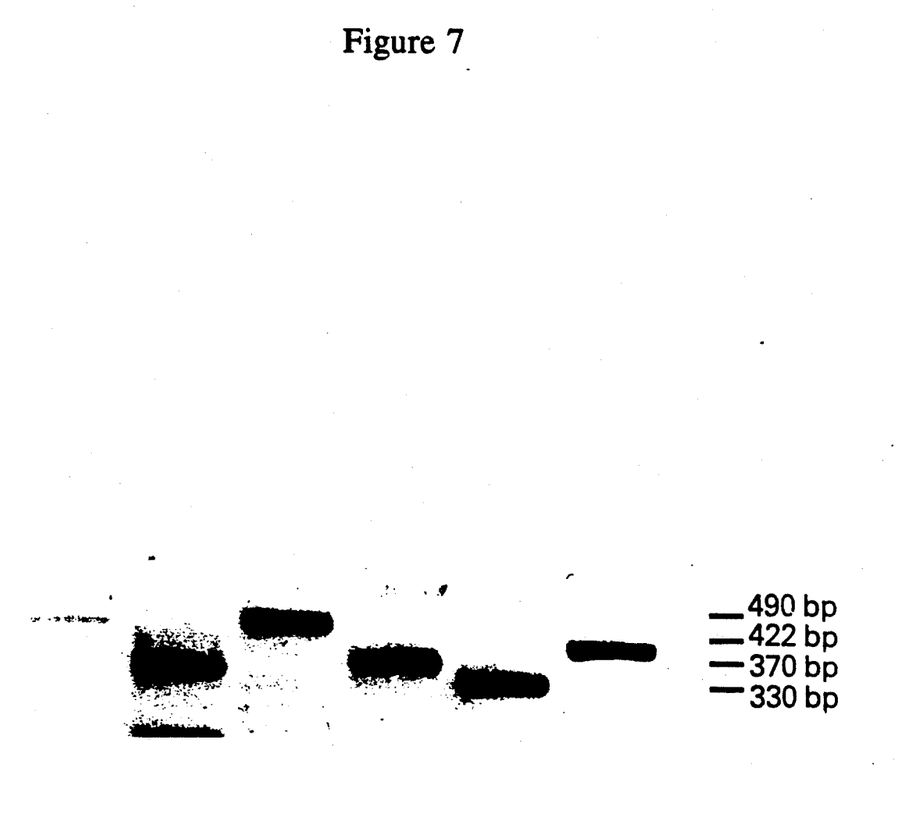
FIG. 7—Detection of amplification products of beta globin mRNA, with different primers on 3% NuSieve agarose gels.
Lane 1: K562 cell line mRNA with—gamma specific primer as a control (489 bp, 10 cycles)
Lane 2: Adult mRNA with alpha specific primer (372 bp, 30 cycles)
Lane 3-6: Adult mRNA with $\beta 4$, $\beta 3$, $\beta 2$, $\beta 1$ different primers (490,370,330,422 bp, 30 cycles)
Figure 8:
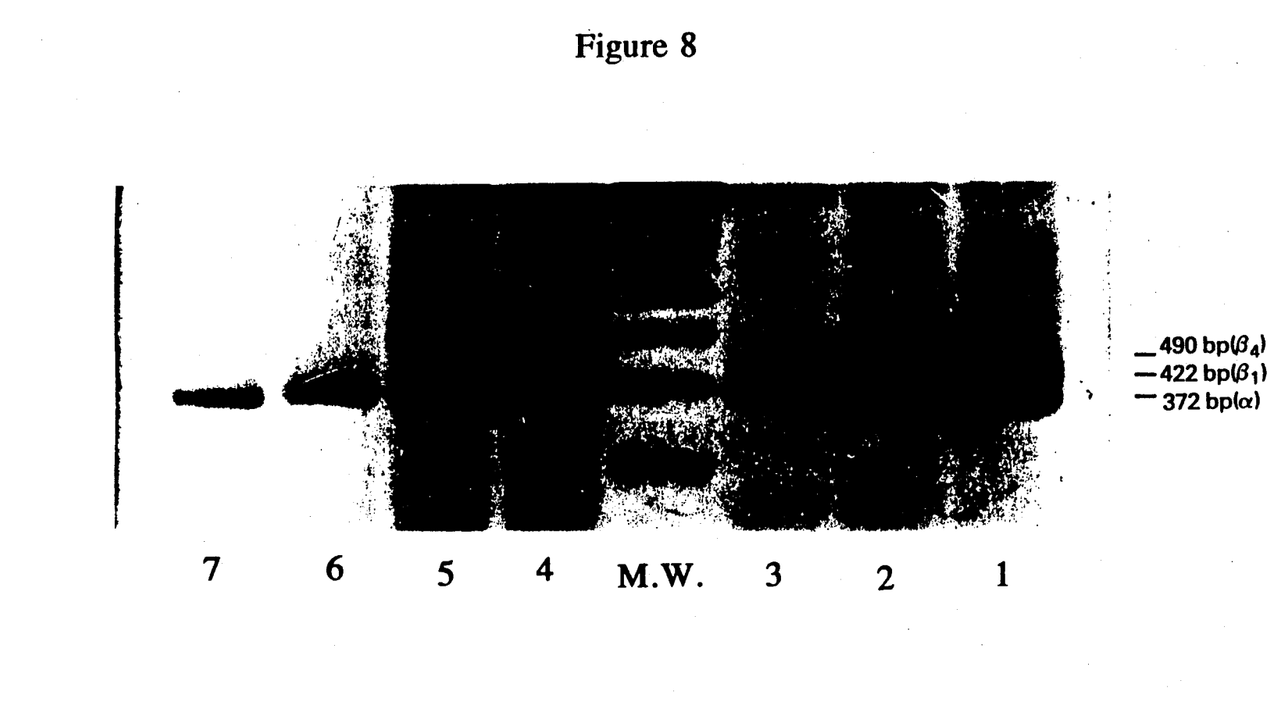
FIG. 8—Detection of co-amplification products of alpha and beta globin mRNAs with different Groups (A and B) of alpha and beta primers.
A Group: alpha (372 bp)+beta 1 (422 bp)
B Group: alpha (372 bp)+beta 4 (490 bp)
Lanes 1,2,4,5: PCR products from normal subjects mRNA with A group of primers (lane 1,2) and the B group of primer (lane 4.5)
Lane 3,6,7: PCR products from a patient with $\beta^o$ thalassemia major with A Group (lane 3) and B Group (lane 6,7) primers
M.W.: 123 bp ladder DNA marker FIG. 9—Detection of PCR products of cDNA amplification with different primers on different cycles in K362 cell line.
Lane 1: primer $\gamma$ and $\alpha$ on cycles 30
Lanes 2,3,4,: primer $\delta$ on cycles 30, 20, 10 respectively
Based on the sensitivity and specificity of PCR products, the number of cycles is established.

The different ratios of α/β from density and radioactivity are also compared in Table 2. It shows that the results are comparable. For the cDNA amplification, two specific groups of oligomer primers, which each spanned the definite exon regions of globin genes were designed and constructed: one was primers α/β4 which directed amplification of 372 bp/490 bp of cDNA fragments; the other was primer β1γ which amplified 422 bp/489 bp cDNA fragments, respectively. The results revealed that the amplified cDNAs each represented a single sharp band on the electrophoretic NuSieve agarose gels (see FIG. 7). FIG. 7 also shows that the 4 sets of β primers we designed are specific to amplify the β globin gene. β1 (422 bp) and β4 (490 bp) combined with the α primer (372 bp), respectively, were chosen to do co-amplification. The result is shown in FIG. 8. It shows that Group B (α+β4) is better than Group A (α+β1). Therefore, Group B primers were used to diagnose β or α thalassemia and primers α (422 bp) and γ (489 bp) (Group II) were used to confirm the above results.

Figure 9:
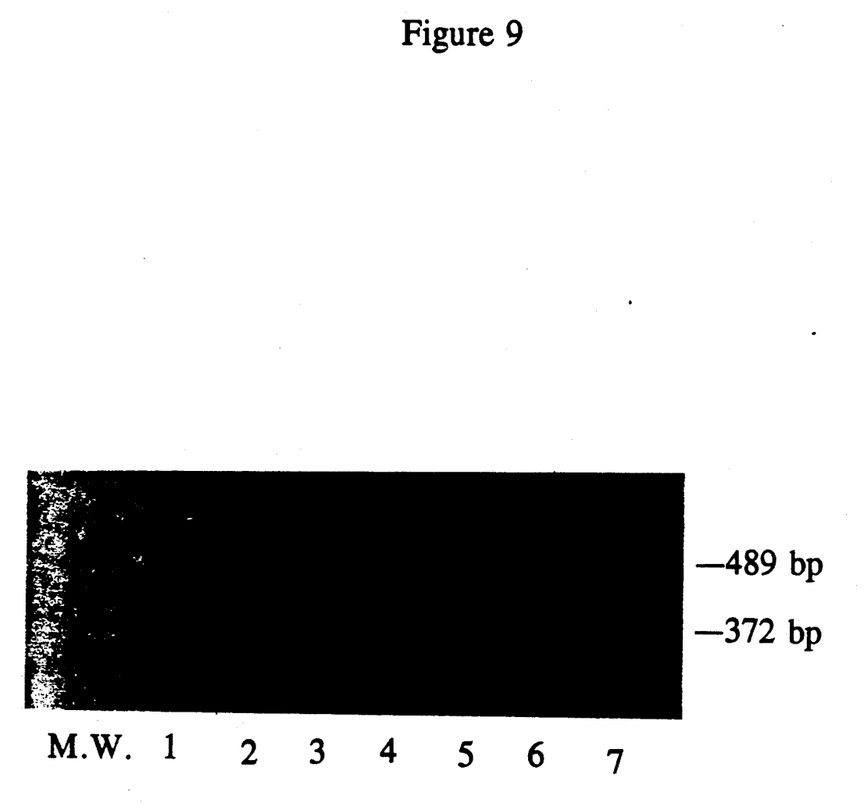

The above primer combination for co-amplification of two different types of globin cDNA had the advantage that two groups of amplified cDNA, e.g., 372 bp/490 bp (Group I) and 422 bp/489 bp (Group II), could be distinguished on the gels (see FIGS. 5 and 6). FIG. 9 shows detection of PCR products of cDNA amplification with different primers on different cycles and the number of cycles is decided based on the sensitivity and specificity of PCR products. These amplified cDNA fragments were subjected to quantitative determination by either densitometer or by counting of the radioactivity. In these experiments, all the amplified cDNAs were so specific that the analyses could be carried out by NuSieve agarose gel without requiring polyacrylamide gel electrophoresis.

Figure 10:
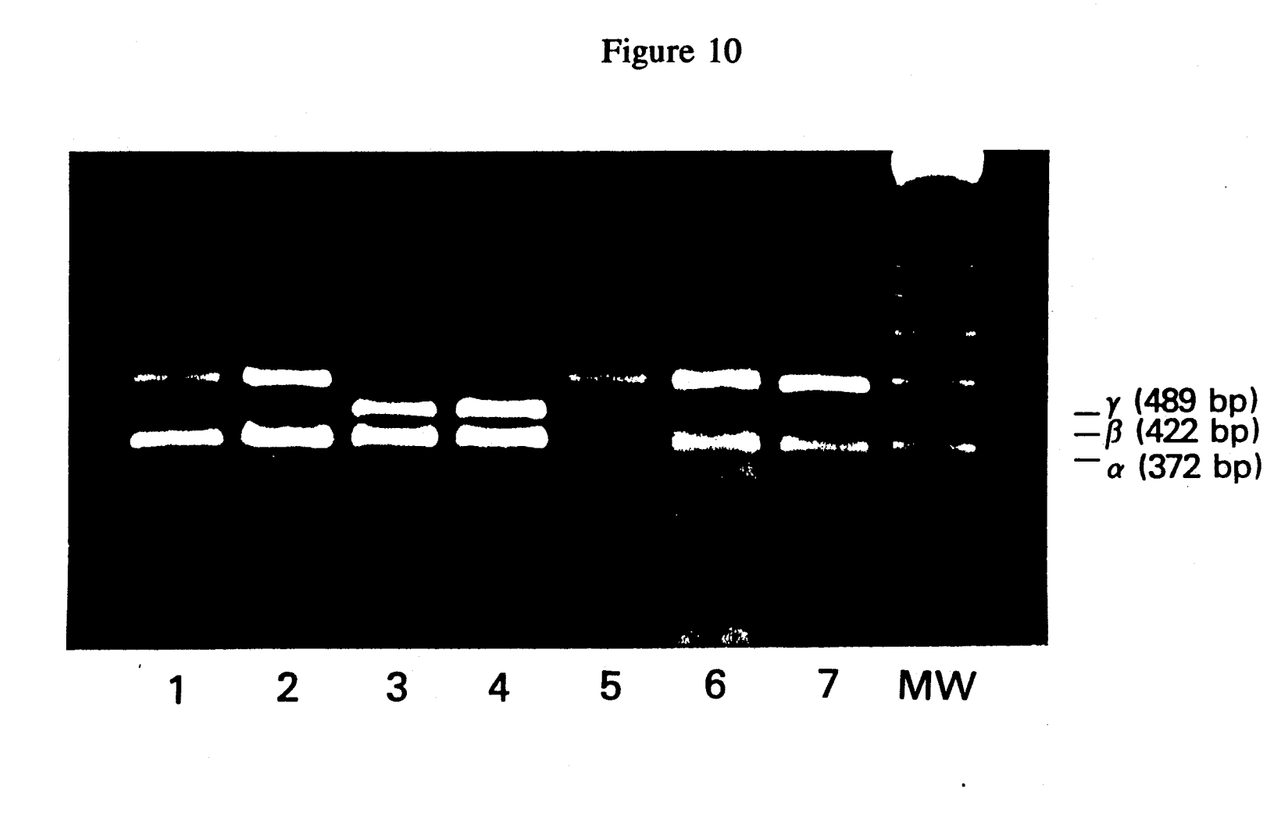
FIG. 10 shows the results of co-amplification of samples from a patient with $\zeta$-thalassemia-1 (--/$\zeta\zeta$) and thalassemia with hydrops fetalis (--/--). There is a reduction in $\zeta/\beta$ ratio in each. As shown in Table 2, this ratio is 0.78 by densitometry and 0.84 by gamma counting in the patient with $\zeta$-thalassemia-1, and essentially zero in the patient with Hydrops fetalis. Thus the diagnosis of $\zeta$-thalassemia is clearly demonstrated by this method.
Figure 11:
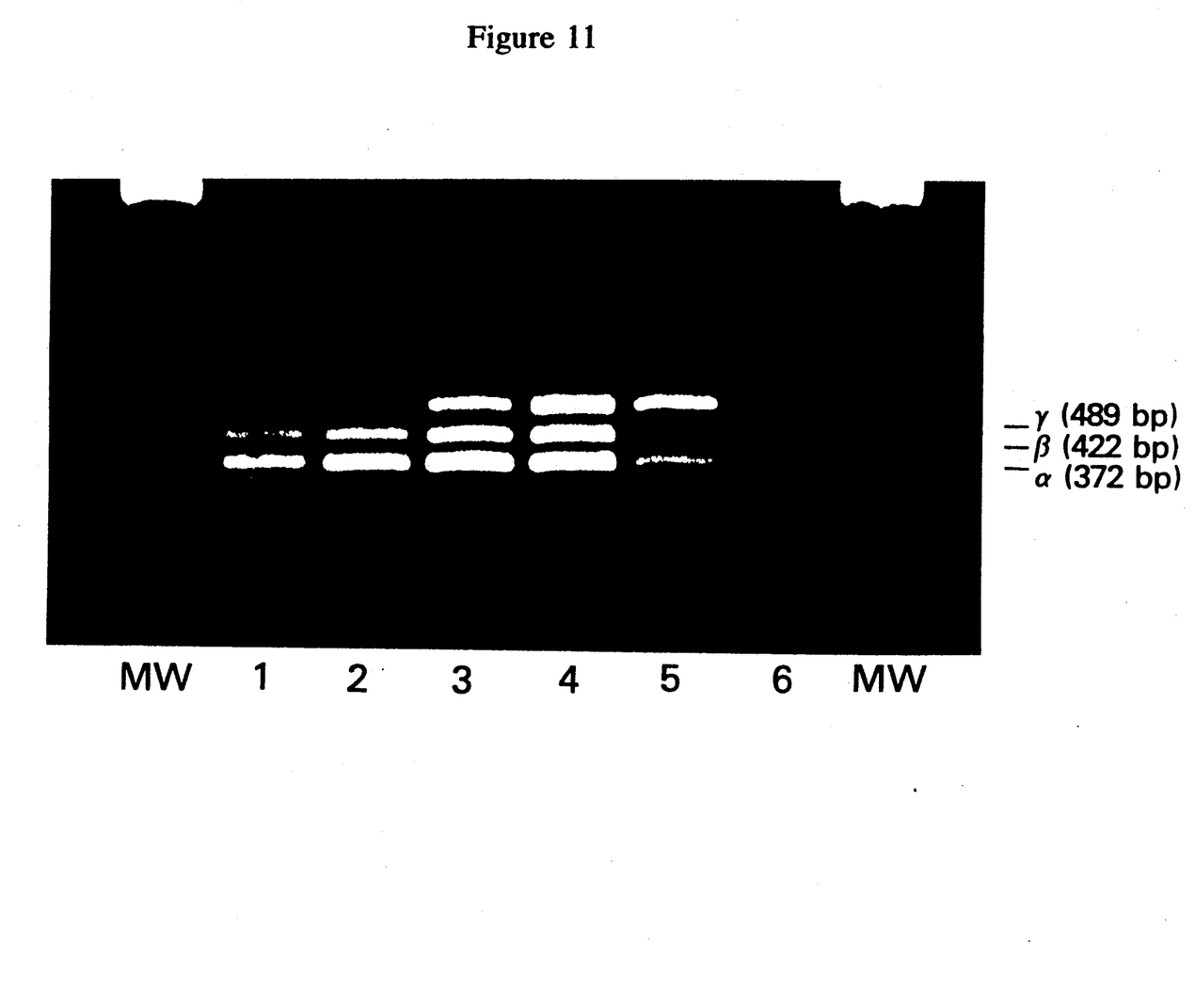
FIG. 11 shows that this method may also be used to follow the increase in $\gamma$-chains in patients with sickle cell anemia or thalassemia treated with hydroxyurea and similar reagents to alter gene expression. It will be seen that during the course of therapy the ratio of $\gamma/\beta$ mRNA increased from 0.65 to 1.27 when followed densitometrically and from 0.50 to 1.09 when measured radioactively.

As shown in FIGS. 10 and 11, patients with α-thalassemia-1 and sickle cell anemia can also be distinguished and followed by the methodology described herein.

In summary, the above experiments demonstrate that the method of the present invention is quite simple, rapid and reliable. By using a simplified RNA extraction, followed by transcriptase and PCR procedures, and the measurements of the relative ratios of different amplified cDNA, it was found that thalassemia can be reliably diagnosed within a few hours.

Figure 1:
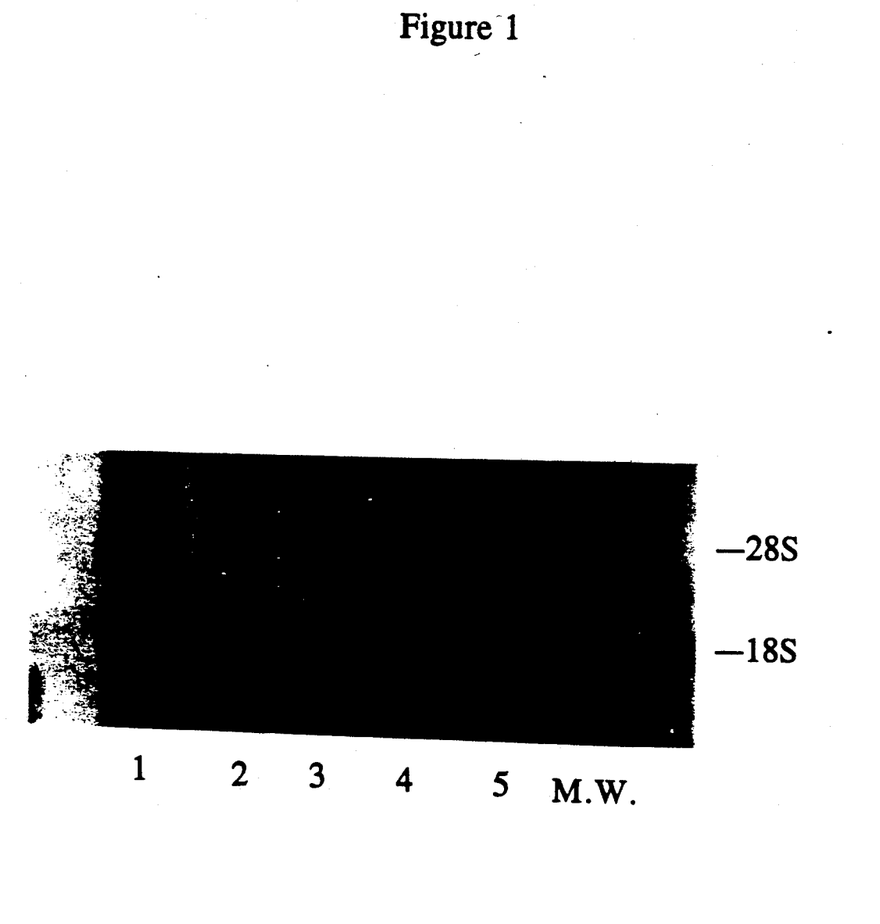
Figure 2A:
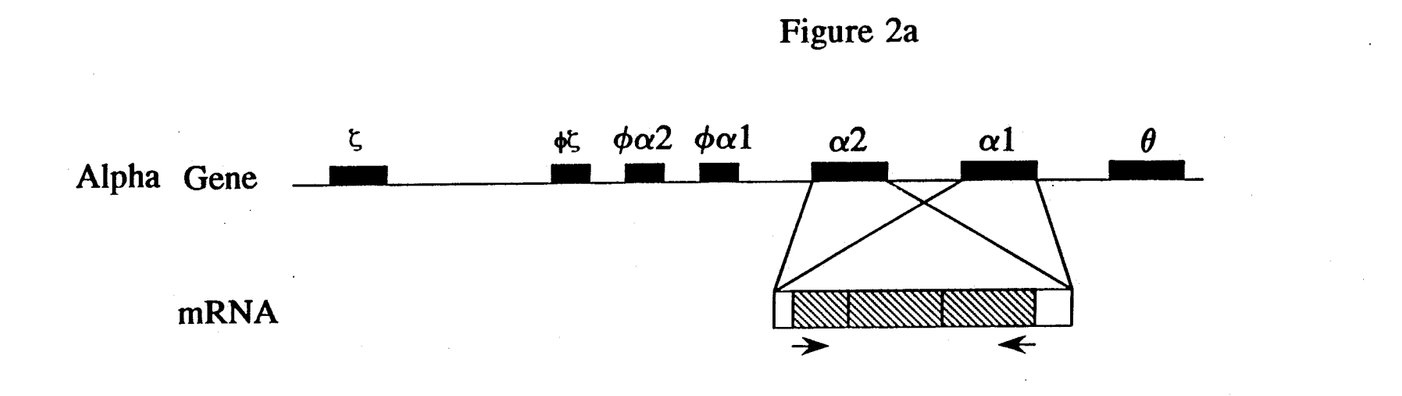
Figure 2B:
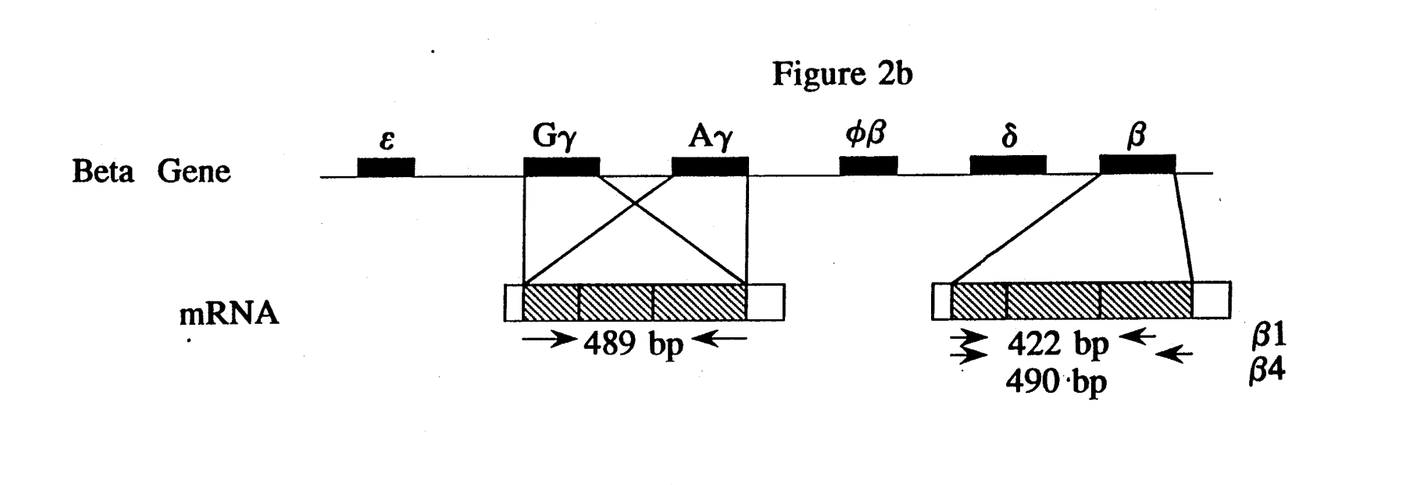

It should be noted that in this diagnostic method, one critical procedure is the RNA extraction and the present invention includes a simple method for this purpose. With the use of the reagent VRC, an inhibitor of RNase, mRNA can be isolated from peripheral reticulocytes and the K652 cell line successfully without the ultra-speed centrifuge process. The results demonstrate that the mRNA isolated by this VRC method was of the appropriate site (FIG. 1).

Determination of absolute amount of mRNA by conventional methods is very complicated and not accurate; moreover, it requires radioactive probes and DNA cloning procedures. In the present method, two groups of internal controls were applied. According to the relative ratios between 372 bp (for α-globin mRNA) and 490 bp (for β-globin mRNA); 422 bp (for β-globin mRNA) and 489 bp (for γ-globin mRNA), various forms of thalassemia can be detected simply and reliably. For example, in $\beta^o$ thalassemia, there is no detectable β-globin mRNA, so the specific amplified β-cDNA disappeared; while in $\beta^+$ thalassemia there is slightly detectable amount of β-globin in mRNA, so a decreased specific amplified β-cDNA appeared. The same principle applies for alpha-thalassemia diagnosis. In addition, the results of the two groups can be used to test each other.

Compared to the currently known molecular methods, the novel technique described herein has various advantages. In the prior art RFLP linkage analysis, at least one patient is required as a reference but in many cases, there is no affected individual available. Hence, the application of RFLP linkage method is restricted to certain families.

The second problem is that radioactive oligomer probes, which are required in the prior art molecular methods, are not easily available. However, in the method of the present invention mRNA transcriptase followed by PCR does not require radioactive probes and thalassemia can be diagnosed easily if the changes of β-globin mRNA occurs, no matter what the nature of the β-thalassemia mutation. The application of photographic film greatly speeds up the total diagnostic process. Hence, it facilitates the diagnosis of β-thalassemia in the developing countries as well.

Recently, promising drug trials and therapeutic approaches have been initiated to preferentially increase the synthesis of fetal hemoglobin in humans. Such strategies would be useful in the treatment of patients afflicted with hemoglobinopathies such as sickle cell anemia and/or β-thalassemia. Of course, the technique described herein for quantitating the relative expression of α, β and γ-mRNA levels can be employed not only to monitor such drug trials, but also to define the therapeutic efficacy and to gather information on the kinetics and mechanism of response. A method for determining the therapeutic efficacy of a treatment for thalassemia, sickle cell disease and other hemoglobinopathies comprises periodically monitoring the increases in the ration of γmRNA to βmRNA as an index of therapeutic response, an increase in said ratio being indicative of an efficacious therapy.

It is understood that the examples and embodiments described herein are for illustrative purposes only and that various modifications or changes in light thereof will be suggested to persons skilled in the art and are to be included within the spirit and purview of this application and scope of the appended claims.

| α 3' | CGGAGGGACCTGTTCAAGGAC |
|---|---| for the α hemoglobin chain, and

| β1 5' | ACACAACTGTGTTCACTAGC |
|---|---|
| β1 3' | AAGTGGGGTGGTCACGTCCGA and |
| β4 5' | ACACAACTGTGTTCACTAGC |
| β4 3' | GCGAAAGAACGACAGGTTAAA |

TABLE 1

The 5' and 3' Primers Used in PCR Reactions

| Primer | Length | Sequence | Position | Length of PCR Products |
|---|---|---|---|---|
| α 5' | 24 | GACAAGACCAACGTCAAGGCCGCC | 56 → 79 | |
| α 3' | 21 | CGGAGGGACCTGTTCAAGGAC | 673 → 693 | 372 bp |
| β 1 5' | 20 | ACACAACTGTGTTCACTAGC | 14 → 33 | |
| β 1 3" | 21 | AAGTGGGGTGGTCACGTCCGA | 1397 → 1417 | 422 bp |
| β 4 5' | 20 | ACACAACTGTGTTCACTAGC | 14 → 33 | |
| β 4 3' | 20 | GCGAAAGAACGACAGGTTAAA | 1479 → 1498 | 490 bp |
| γ 5' | 21 | ACTCGCTTCTGGAACGTCTGA | 3 → 23 | |
| γ 3' | 21 | TCACGGGACAGGAGGTCTATG | 1477 → 1497 | 489 bp |

TABLE 2

The ratio of α and β mRNA ascertained from density and radioactivity measurements.

| | No. | Densitometry Scan α/β Ratio | | Gamma Counts α/β Ratio | |
|---|---|---|---|---|---|
| | | mean (SE) | Range | mean (SE) | Range |
| β° thalassemia major | 5 | >100.00* | | 39.58 (±15.66) | 14.4–100.00 |
| β+ thalassemia major | 2 | 4.10 | 3.6–4.5 | 6.10 | 5.2–7.2 |
| α thalassemia-1 (—/αα) | 1 | 0.78 | | 0.84 | |
| α thalassemia (—/—) Bart's Hydrops Fetalis | 1 | 0.00 | | 0.00 | |
| Normal Adults | 10 | 1.33 (±0.04) | 1.07–1.49 | 1.14 (±0.05) | 0.9–1.35 |

*No β band and no β peak.

TABLE 3

The ratio of α/β+γ and γ/β mRNA ascertained from density and radioactivity measurements in a patient with sickle cell anemia treated with hydroxyurea

| | Densitometry Scan | | Gamma Counts | |
|---|---|---|---|---|
| | α/β+γ | γ/β | α/β+γ | γ/β |
| Normal Adults | 1.34 | 0.00* | 1.40 | 0.09 |
| Sickle Cell Anemia (0 day)* | 0.91 | 0.65 | 1.30 | 0.50 |
| Sickle Cell Anemia (57 days) | 0.66 | 0.97 | 1.00 | 0.74 |
| Sickle Cell Anemia (88 days) | 0.52 | 1.27 | 1.20 | 1.05 |

*γmRNA too low, cannot measure on densitometer.
*Numbers for patient indicate hydroxyurea treatment day.

What is claimed is:

1. A method for diagnosing thalassemia, comprising the steps of:
   (a) extracting with an RNase inhibitor reagent an mRNA sample from the peripheral blood of an individual suspected of thalassemia;
   (b) preparing a cDNA sample complementary to the mRNA obtained in step (a);
   (c) amplifying the cDNA obtained from step (b) by polymerase chain reaction using thalassemia cDNA-specific primers selected from the group consisting of:

| α 5' | GACAAGACCAACGTCAAGGCCGCC |
|---|---| for the β hemoglobin chain and then
   (d) determining radiometric or densitometric ratio between α and β hemoglobin chain mRNas by the ratio between corresponding amplified cDNA obtained in step (c), a ratio greater than 100 being indicative of β° thalassemia major, a ratio in the range of 3.6 to 4.5 being indicative of β+ thalassemia major and a ratio of less than 1.0 being indicative of α thalassemia.

2. The method of claim 1 wherein a radioactive purine or pyrimidine triphosphate base is added to facilitate quantitation of the product obtained from step (c).

3. The method of claim 2 wherein said base is $B2P$-dCTP.

4. The method of claim 3 wherein a radiometric ratio between α and β mRNA in the range of 14–100 is indicative of β° thalassemia major.

5. The method of claim 3 wherein a radiometric ratio between α and β mRNA in the range of 5.2–7.2 is indicative of β+ thalassemia major and a range less than 1.0 is indicative of α thalassemia.

6. A method for determining the therapeutic efficacy of a treatment for thalassemia, sickle cell disease and other hemoglobinopathies, comprising periodically monitoring the increases in the ratio of γmRNA to βmRNA as an index of therapeutic response, an increase in said ratio being indicative of an efficacious therapy.

7. The method of claim 1 wherein the RNase inhibitor is Vanadyl Ribonucleoside Complex.

* * * * *